US010130820B2

(12) United States Patent
Bobgan et al.

(10) Patent No.: US 10,130,820 B2
(45) Date of Patent: Nov. 20, 2018

(54) HEADER CORE FIXATION DESIGN FOR AN IMD

(71) Applicant: Cardiac Pacemakers, Inc., St. Paul, MN (US)

(72) Inventors: Jean M. Bobgan, Maple Grove, MN (US); James M. English, Cahir (IE); David P. Stieper, North Branch, MN (US); Richard Percy, Leamlara (IE); Patrick J. Barry, North St. Paul, MN (US); Ernest Beaudet, Stillwater, MN (US); Matthew Couri, Maple Grove, MN (US); Mark A. Lamberty, Cottage Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 47 days.

(21) Appl. No.: 15/242,470

(22) Filed: Aug. 19, 2016

(65) Prior Publication Data
US 2017/0050032 A1 Feb. 23, 2017

Related U.S. Application Data

(60) Provisional application No. 62/307,099, filed on Mar. 11, 2016, provisional application No. 62/207,909, filed on Aug. 20, 2015.

(51) Int. Cl.
| | |
|---|---|
| *A61N 1/372* | (2006.01) |
| *A61N 1/375* | (2006.01) |
| *A61B 5/00* | (2006.01) |
| *A61B 5/0205* | (2006.01) |
| *A61B 5/11* | (2006.01) |
| *A61B 7/04* | (2006.01) |
| *A61N 1/362* | (2006.01) |
| *A61N 1/39* | (2006.01) |

(52) U.S. Cl.
CPC ........ *A61N 1/37217* (2013.01); *A61B 5/0008* (2013.01); *A61B 5/0022* (2013.01); *A61B 5/0205* (2013.01); *A61B 5/11* (2013.01); *A61B 5/1112* (2013.01); *A61B 5/1118* (2013.01); *A61B 7/04* (2013.01); *A61N 1/362* (2013.01); *A61N 1/375* (2013.01); *A61N 1/3956* (2013.01)

(58) Field of Classification Search
None
See application file for complete search history.

(56) References Cited

U.S. PATENT DOCUMENTS

| | | | |
|---|---|---|---|
| 5,643,328 A | 7/1997 | Cooke et al. | |
| 8,843,215 B2 * | 9/2014 | Eck | ........................ A61N 1/362 607/119 |
| 8,989,872 B2 | 3/2015 | Prasannakumar et al. | |

(Continued)

OTHER PUBLICATIONS

International Search Report and Written Opinion issued in PCT/US2016/047922, dated Oct. 26, 2016, 10 pages.

*Primary Examiner* — Erica Lee
(74) *Attorney, Agent, or Firm* — Faegre Baker Daniels LLP

(57) ABSTRACT

Aspects of the present disclosure are directed toward apparatuses, systems, and methods that may comprise a medical device having a header, a core assembly, and a scaffold assembly. The scaffold assembly may be configured to interface with the core assembly and position and support one or more circuit component relative to one or more other circuit components.

9 Claims, 14 Drawing Sheets

(56) References Cited

U.S. PATENT DOCUMENTS

| | | | |
|---|---|---|---|
| 2006/0069322 A1* | 3/2006 | Zhang | A61B 5/04011 |
| | | | 600/512 |
| 2006/0241702 A1 | 10/2006 | Gillberg | |
| 2006/0241715 A1* | 10/2006 | Sprain | A61N 1/375 |
| | | | 607/37 |
| 2012/0322317 A1* | 12/2012 | Seeley | A61N 1/3752 |
| | | | 439/668 |
| 2013/0150937 A1* | 6/2013 | Kane | A61N 1/05 |
| | | | 607/116 |
| 2014/0135882 A1 | 5/2014 | Prasannakumar et al. | |
| 2015/0094792 A1* | 4/2015 | Kane | A61N 1/362 |
| | | | 607/122 |

* cited by examiner

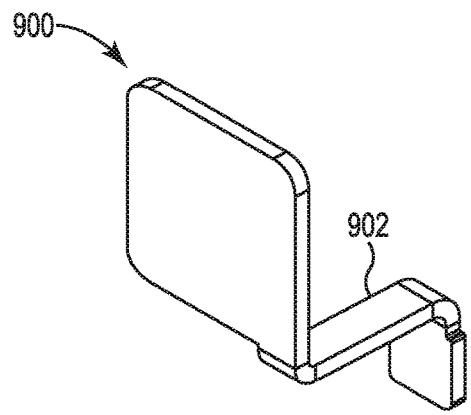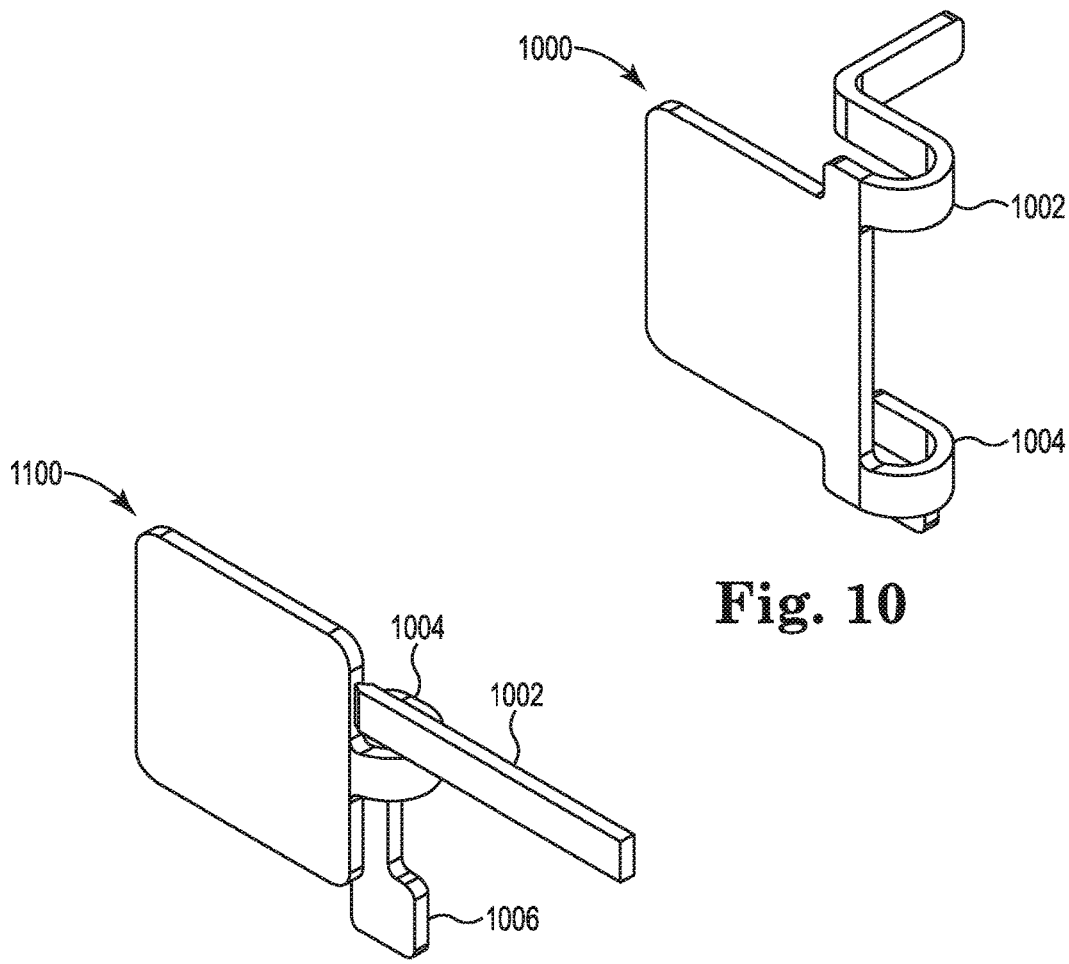
Fig. 9
Fig. 10
Fig. 11

HEADER CORE FIXATION DESIGN FOR AN IMD

CROSS-REFERENCE TO RELATED APPLICATION

This application claims priority to Provisional Application Nos. 62/207,909, filed Aug. 20, 2015, and 62/307,099, filed Mar. 11, 2016, both of which are herein incorporated by reference in their entirety.

TECHNICAL FIELD

Embodiments of the present invention relate to medical devices and systems for sensing physiological parameters and/or delivering therapy. More specifically, embodiments of the invention relate to devices and methods for header core fixation in an implantable medical device.

BACKGROUND

Implantable medical devices (IMDs) may be configured to sense physiological parameters and/or provide therapy and may include one or more electrodes for performing aspects of these functions. IMDs may also include antennas for communicating with other devices. Conventionally, devices such as programmers and wands have been used to cause IMDs to take various actions such as for example, marking recordings of physiological parameters, initiating communications with other devices, and the like.

SUMMARY

In Example 1, a medical device comprising: a first circuit component and a second circuit component arranged within the header; and a scaffold assembly configured to position and support the first circuit component relative to the second circuit component.

In Example 2, the medical device of Example 1, further comprising a header and a core assembly, wherein the scaffold assembly is arranged within the header and configured to interface with the core assembly, and the core assembly comprises a first end portion, a second end portion, and an intermediate section therebetween.

In Example 3, the medical device of Example 2, wherein the first end portion of the core assembly comprises first mating feature, the scaffold assembly comprises a second mating feature, and the first mating feature is complimentary to the second mating feature.

In Example 4, the medical device of either of Examples 2-3, wherein the first end portion of the core assembly comprises at least one conduit to the intermediate section of the core assembly.

In Example 5, the medical device of Example 4, further comprising an integrated circuit arranged within the intermediate section of the core assembly and at least one electrical connector, and wherein the at least one conduit is configured to provide a feedthrough for the at least one electrical connector, and the at least one electrical connector is configured to electrically connect one of the first circuit component and the second circuit component to the integrated circuit.

In Example 6, the medical device of any of Example 2, wherein the header comprises an internal portion and an external portion, and the interior portion comprises a first surface and a second surface.

In Example 7, the medical device of any of Examples 1-6, wherein the first circuit component comprises an antenna, and the second circuit component comprises an electrode having a break-away section releasably secured to the electrode via a break-away tab, and wherein the break-away section is configured to align with an alignment notch defined in the scaffold assembly.

In Example 8, the medical device of Example 7, wherein the scaffold assembly is configured to support and position the electrode flush with the first surface of the interior portion of the header, and the break-away section is configured to be manipulated so as to break or split from the electrode.

In Example 9, the medical device of Example 7, wherein the scaffold assembly includes a frontward facing portion and a rearward facing portion, and wherein the frontward facing portion is arranged to support the electrode and the rearward facing portion contacts the second surface of the interior portion of the header.

In Example 10, the medical device of any of Examples 1-9, wherein the scaffold assembly is configured to arrange the first circuit component to at least partially surround the second circuit component.

In Example 11, a system comprising: a medical device, configured to be implanted within a body of a patient, the implantable medical device, the medical device comprises a header and a core assembly; an antenna arranged within the header and configured to communicate data and an electrode arranged within the header and configured to collect data; and a scaffold assembly arranged within the header and configured to interface with the core assembly and position and support the antenna relative to the electrode.

In Example 12, the system of Example 11, further comprising a receiving device configured to receive the data communicated from the implantable medical device, and wherein the scaffold assembly includes a frontward facing portion, a rearward facing portion, an upper portion, and a lower portion, and wherein the frontward facing portion is arranged to support the electrode, the rearward facing portion contacts the second surface of the interior portion of the header, and the upper portion is configured to support the antenna.

In Example 13, the system of Example 12, wherein the lower portion includes a mating feature configured to interface with the core assembly.

In Example 14, the system of Example 13, wherein the mating feature is arranged along the rearward facing portion of the scaffold assembly.

In Example 15, the system of any of Examples 11-14, wherein the implantable medical device further comprises an integrated circuit arranged within the core assembly and is configured to prompt the antenna to communicate with the receiving device.

In Example 16, an implantable medical device comprising: a header and a core assembly; a first circuit component and a second circuit component arranged within the header; and a scaffold assembly arranged within the header and configured to interface with the core assembly and position and support the first circuit component relative to the second circuit component.

In Example 17, the medical device of Example 16, wherein the core assembly comprises a first end portion, a second end portion, and an intermediate section therebetween, and the first end portion, and the electrode comprises a break-away section releasably secured to the electrode via a break-away tab, and wherein the break-away section is configured to align with an alignment notch defined in the scaffold assembly.

In Example 18, the medical device of Example 17, wherein the first end portion of the core assembly comprises first mating feature, and the scaffold assembly comprises a second mating feature, and the first mating feature is complimentary to the second mating feature, and the break-away section is configured to be manipulated so as to break or split from the electrode.

In Example 19, the medical device of Example 16, wherein the first end portion of the core assembly comprises at least one conduit to the intermediate section of the core assembly.

In Example 20, the medical device of Example 19, wherein the scaffold assembly includes a frontward facing portion, a rearward facing portion, the least one conduit is arranged on a rearward facing portion side of the scaffold assembly, and the second circuit component is arranged on a frontward facing portion side of the scaffold assembly.

In Example 21, the medical device of Example 19, further comprising at least one electrical connector, and wherein the at least one conduit is configured to provide a feedthrough for the at least one electrical connector.

In Example 22, the medical device of Example 21, further comprising an integrated circuit arranged within the intermediate section of the core assembly, and the at least one electrical connector is configured to electrically connect one of the first circuit component and the second circuit component to the integrated circuit.

In Example 23, the medical device of Example 16, wherein the header comprises an internal portion and an external portion, and the interior portion comprises a first surface and a second surface.

In Example 24, the medical device of Example 23, wherein the first circuit component comprises an antenna, and the second circuit component comprises an electrode.

In Example 25, the medical device of Example 24, wherein the scaffold assembly is configured to support and position the electrode flush with the first surface of the interior portion of the header.

In Example 26, the medical device of Example 24, wherein the scaffold assembly includes a frontward facing portion and a rearward facing portion, wherein the frontward facing portion is arranged to support the electrode and the rearward facing portion contacts the second surface of the interior portion of the header.

In Example 27, a system comprising: a medical device, configured to be implanted within the body of a patient, the implantable medical device comprises a header and a core assembly, an antenna arranged within the header and configured to communicate data, and an electrode arranged within the header and configured to collect data; a scaffold assembly arranged within the header and configured to interface with the core assembly and position and support the antenna relative to the electrode; and a receiving device configured to receive the data communicated from the implantable medical device.

In Example 28, the system of Example 26, wherein the implantable medical device comprises at least one of an implantable diagnostic monitor (IDM), a cardiac pacemaker, an implantable cardioverter defibrillator (ICD) device, and a cardiac resynchronization therapy (CRT) device.

In Example 29, the system of Example 26, wherein the scaffold assembly includes a frontward facing portion, a rearward facing portion, an upper portion, and a lower portion, and wherein the frontward facing portion is arranged to support the electrode, the rearward facing portion contacts the second surface of the interior portion of the header, and the upper portion is configured to support the antenna.

In Example 30, the system of Example 26, wherein the lower portion includes a mating feature configured to interface with the core assembly.

In Example 31, the system of Example 30, wherein the mating feature is arranged along the rearward facing portion of the scaffold assembly.

In Example 32, the system of Example 27, wherein the implantable medical device further comprises an integrated circuit arranged within the core assembly, wherein the integrated circuit is configured to prompt the antenna to communicate with the receiving device.

In Example 33, a method comprising: interfacing a scaffold assembly with a core assembly of an implantable medical device; arranging a first circuit component and a second circuit component on portions of the scaffold assembly, the scaffold assembly being configured to position and support the first circuit component relative to the second circuit component; and arranging a header assembly over and around the scaffold assembly and interfacing the header assembly with the core assembly.

In Example 34, the method of Example 33, further comprising electrically connecting the first circuit component and the second circuit component to an integrated circuit arranged within the core assembly.

In Example 35, the method of Example 34, wherein electrically connecting the first circuit component and the second circuit component comprises welding the first circuit component and the second circuit to respective electrical connectors coupled to the integrated circuit.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 9 is a perspective view of an example electrode, in accordance with embodiments of the disclosure.

FIG. 10 is a perspective view of another example electrode, in accordance with embodiments of the disclosure.

FIG. 11 is a perspective view of another example electrode, in accordance with embodiments of the disclosure.

Figure 1:
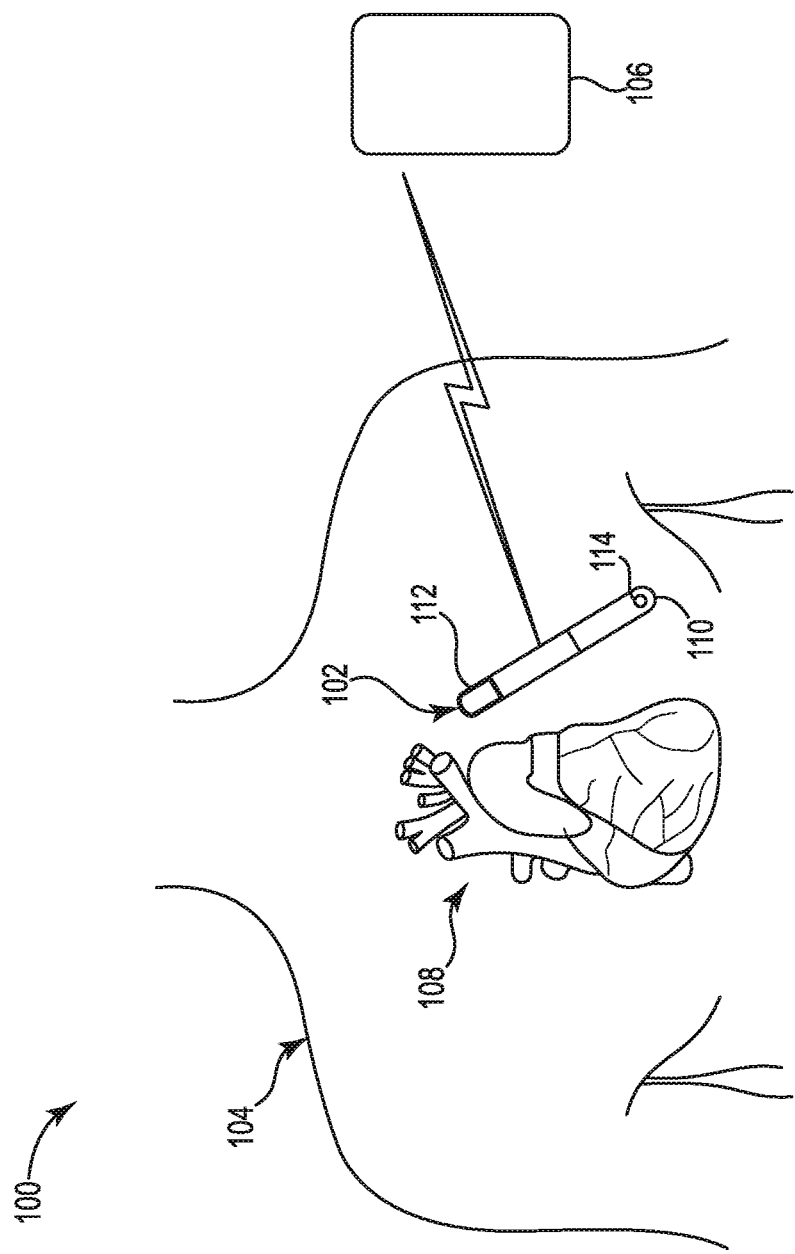
FIG. 1 is a schematic illustration of a system having an implantable medical device (IMD) and a receiving device, in accordance with embodiments of the disclosure.

While the disclosed subject matter is amenable to various modifications and alternative forms, specific embodiments have been shown by way of example in the drawings and are described in detail below. The intention, however, is not to limit the disclosed subject matter to the particular embodiments described. On the contrary, the disclosed subject matter is intended to cover all modifications, equivalents, and alternatives falling within the scope of the disclosed subject matter as defined by the appended claims.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

FIG. 1 is a schematic illustration of a system 100 including an implantable medical device (IMD) 102 implanted within a patient's body 104 and configured to communicate with a receiving device 106. In embodiments, the IMD 102 may be implanted subcutaneously within an implantation location or pocket in the patient's chest or abdomen and may be configured to monitor (e.g., sense and/or record) physiological parameters associated with the patient's heart 108. In embodiments, the IMD 102 may be an implantable cardiac monitor (ICM) (e.g., an implantable diagnostic monitor (IDM), an implantable loop recorder (ILR), etc.) configured to record physiological parameters such as, for example, one or more cardiac activation signals, heart sounds, blood pressure measurements, oxygen saturations, and/or the like. In embodiments, the IMD 102 may be configured to monitor physiological parameters that may include one or more signals indicative of a patient's physical activity level and/or metabolic level, such as an acceleration signal. In embodiments, the IMD 102 may be configured to monitor physiological parameters associated with one or more other organs, systems, and/or the like. The IMD 102 may be configured to sense and/or record at regular intervals, continuously, and/or in response to a detected event. In embodiments, such a detected event may be detected by one or more sensors of the IMD 102, another IMD (not shown), an external device (e.g., the receiving device 106), and/or the like. In addition, the IMD 102 may be configured to detect a variety of physiological signals that may be used in connection with various diagnostic, therapeutic, and/or monitoring implementations. For example, the IMD 102 may include sensors or circuitry for detecting respiratory system signals, cardiac system signals, and/or signals related to patient activity. In embodiments, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

For purposes of illustration, and not of limitation, various embodiments of devices that may be used to record physiological parameters in accordance with the present invention are described herein in the context of IMDs that may be implanted under the skin in the chest region of a patient.

As shown, the IMD 102 may include a housing 110 having two electrodes 112 and 114 coupled thereto. According to embodiments, the IMD 102 may include any number of electrodes (and/or other types of sensors such as, e.g., thermometers, barometers, pressure sensors, optical sensors, motion sensors, and/or the like) in any number of various types of configurations, and the housing 110 may include any number of different shapes, sizes, and/or features. In embodiments, the IMD 102 may be configured to sense physiological parameters and record the physiological parameters. For example, the IMD 102 may be configured to activate (e.g., periodically, continuously, upon detection of an event, and/or the like), record a specified amount of data (e.g., physiological parameters) in a memory, and communicate that recorded data to a receiving device 106. In the case of an IDM, for example, the IMD 102 may activate, record cardiac signals for a certain period of time, deactivate, and activate to communicate the recorded signals to the receiving device 106.

In various embodiments, the receiving device 106 may be, for example, a programmer, controller, patient monitoring system, and/or the like. Although illustrated in FIG. 1 as an external device, the receiving device 106 may include an implantable device configured to communicate with the IMD 102 that may, for example, be a control device, another monitoring device, a pacemaker, an implantable defibrillator, a cardiac resynchronization therapy (CRT) device, and/or the like, and may be an implantable medical device known in the art or later developed, for providing therapy and/or diagnostic data about the patient and/or the IMD 102.

In various embodiments, the IMD 102 may be a pacemaker, an implantable cardioverter defibrillator (ICD) device, or a cardiac resynchronization therapy (CRT) device. In various embodiments, the IMD 102 may include both defibrillation and pacing/CRT capabilities (e.g., a CRT-D device).

The system 100 may be used to implement coordinated patient measuring and/or monitoring, diagnosis, and/or therapy in accordance with embodiments of the invention. The system 100 may include, for example, one or more patient-internal medical devices, such as an IMD 102, and one or more patient-external medical devices, such as receiving device 106. In embodiments, the receiving device 106 may be configured to perform monitoring, and/or diagnosis and/or therapy functions external to the patient (i.e., not invasively implanted within the patient's body). The receiving device 106 may be positioned on the patient, near the patient, or in any location external to the patient.

In embodiments, the IMD 102 and the receiving device 106 may communicate through a wireless link. For example, the IMD 102 and the receiving device 106 may be coupled through a short-range radio link, such as Bluetooth, IEEE 802.11, and/or a proprietary wireless protocol. The communications link may facilitate uni-directional and/or bi-directional communication between the IMD 102 and the receiving device 106. Data and/or control signals may be transmitted between the IMD 102 and the receiving device 106 to coordinate the functions of the IMD 102 and/or the receiving device 106. In embodiments, patient data may be downloaded from one or more of the IMD 102 and the receiving device 106 periodically or on command. The physician and/or the patient may communicate with the IMD 102 and the receiving device 106, for example, to acquire patient data or to initiate, terminate, or modify recording and/or therapy.

The illustrative system 100 shown in FIG. 1 is not intended to suggest any limitation as to the scope of use or functionality of embodiments of the subject matter disclosed throughout this disclosure. Neither should the illustrative system 100 be interpreted as having any dependency or requirement related to any single component or combination of components illustrated in FIG. 1. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

Figure 2:
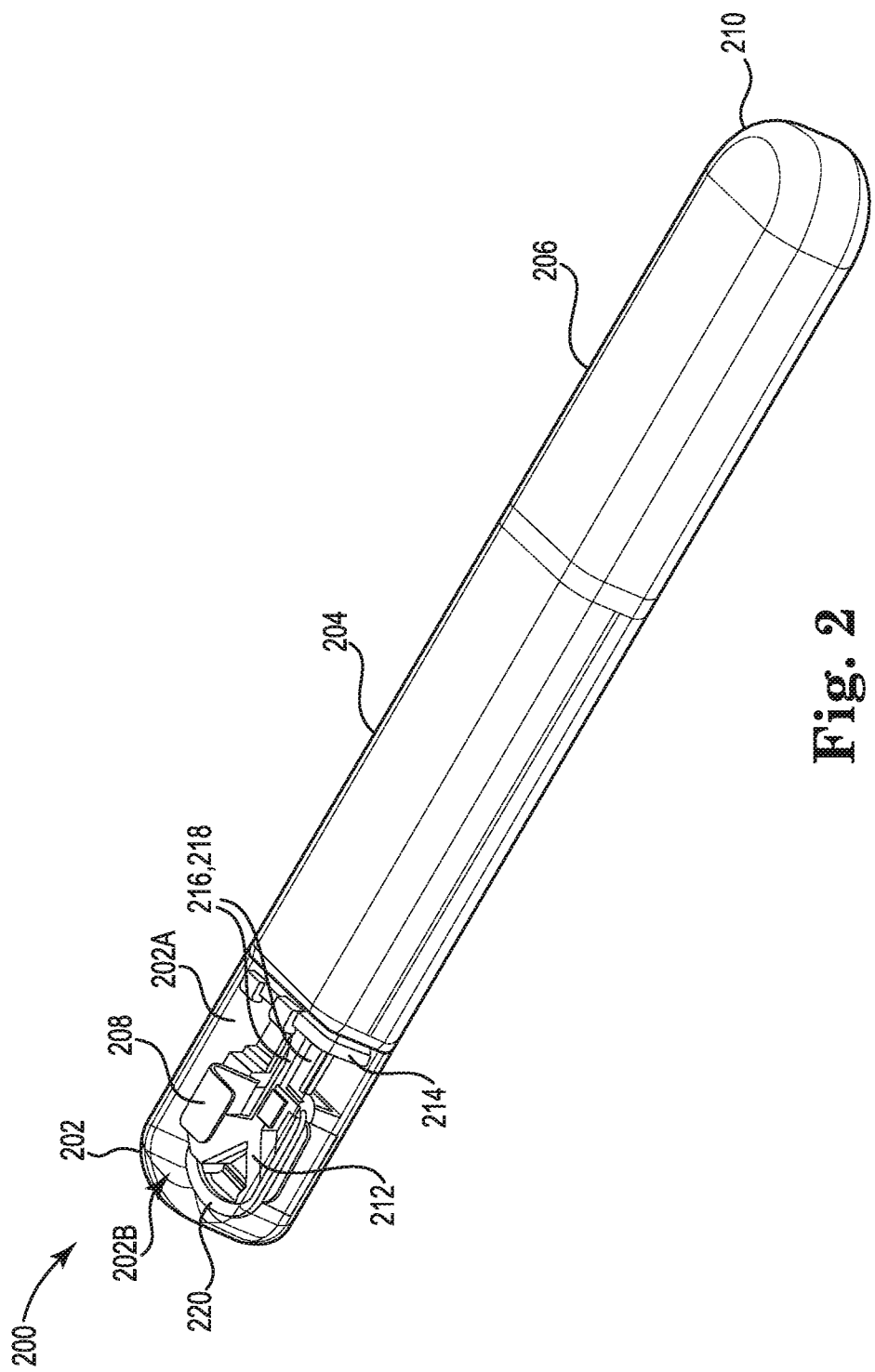
FIG. 2 is a perspective view of an IMD, in accordance with embodiments of the disclosure.

FIG. 2 is a perspective view of an implantable medical device (IMD) 200, in accordance with embodiments of the invention. The IMD 200 may be, or may be similar to, the IMD 102 depicted in FIG. 1. As shown, the IMD 200 may include a header 202 arranged at or near an end (first) portion of the core assembly 204. The header 202 may also include a scaffold assembly 212 configured to position and support the circuit components. In addition, the scaffold assembly 212 may be coupled and/or secured to the core assembly 204 of the IMD 200. The core assembly 204 forms an intermediate section of the IMD 200. Further, the IMD 200 may include a battery 206 arranged near an end (second) portion of the core assembly 204.

The header 202 includes an exterior surface 202A that encloses an interior region 202B. The header 202 may house various circuitry components within its interior. The exterior surface 202A may contact a patient's bodily tissue when the IMD 200 is subcutaneously implanted in an implantation location or pocket in the patient's chest or abdomen. The interior region 202B of the header 202 may provide a space and house the core assembly 204 and circuit components positioned and supported by the scaffold assembly 212. As shown, the IMD 202 may include electrodes 208, 210, including one electrode 208 within the header 202. In order to enable sensing of physiological parameters within the patient, the electrode 208 may be positioned to be flush with the interior region 202B of the header 202. In other instances, the electrode 208 may be positioned by the scaffold assembly 212 to form a portion of the exterior surface 202A of the header 202.

In certain instances, functionality of the circuitry components housed within the header 202 may depend on the arrangement or positioning of the circuitry components within the header 202. More specifically, unintended or uncontrolled movement of one or more circuitry components may disengage the circuitry components from integrated (control) circuitry (powered by the battery 206) that is contained within the core assembly 204 of the IMD 200 (as is discussed in further detail below). Further and in certain instances, the one or more circuitry components may include an antenna 220 in addition to the electrode 208. As a result, a desired arrangement and/or positioning of the circuitry components within the header 202 may be required. In certain instances, for example, the electrode 208 must be on the surface of the header 202 and have contact with tissue. Further, it may be beneficial to position the antenna 220 closer to the skin side (e.g., exterior side of a patient's body) of the header 202 so there is less body tissue to transmit through. In addition, to avoid shorting of the electrode 208 and antenna 220, the scaffold assembly 212 may provide adequate spacing therebetween. This may provide for controlled and predictable performance of the antenna 220. In certain instances, it may be beneficial to form the scaffold assembly 212 of a non-conductive and/or insulative material to avoid capacitive coupling between the antenna 220 and electrode 208.

As shown in FIG. 2, the scaffold assembly 212 is provided within the header 200 and supports the electrode 208. Along with the electrode 208, the scaffold assembly 212 also supports and positions one or more additional circuit components, such as the electrode 208 and the antenna 220. The scaffold assembly 212 interfaces with a portion 214 of the core assembly 204. In addition, the scaffold assembly 212 may provide a throughput or alley for interconnects 216, 218. The interconnects 216, 218 may be configured to connect the circuitry components, such as the electrode 208 and the antenna 220 positioned and supported by the scaffold assembly 212, to the integrated circuitry contained within the core assembly 204 of the IMD 200.

Figure 3A:
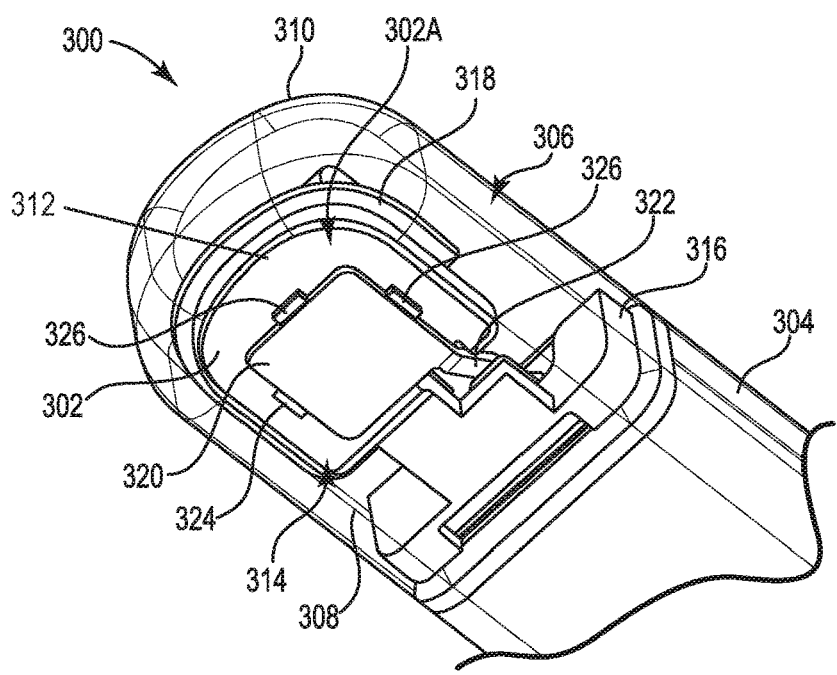
FIG. 3A is a front-facing view of a header and scaffold assembly, in accordance with embodiments of the disclosure.

FIG. 3A is a front-facing perspective view of a header 300 and scaffold assembly 302, in accordance with embodiments of the disclosure. The scaffold assembly 302 includes a first surface 302A, and a second surface 302B, as shown in greater detail in FIG. 3B. FIG. 3A also shows a portion of a core assembly 304. As discussed above with reference to FIG. 2, the header 300, scaffold assembly 302, and core assembly 304 may form portions of an IMD. As such, an end portion and a portion of an intermediate section of the core assembly 304 is shown in FIG. 3A. Further, additional elements of the IMD may be included at the other end portion of the core assembly 304 (not shown). These elements may include a battery and an electrode.

The header 300 includes a housing 306 that separates the internal portions of the header 300, including the scaffold assembly 302, from a patient's tissue when the header 300 and scaffold assembly 302 is implanted as part of the IMD (e.g., as shown in FIG. 2 and as discussed above). The housing 306 includes two internal surfaces: a first surface 308 and a second surface 310. The scaffold assembly 302 includes an upper portion 312, an intermediate portion 314, and a lower portion 316.

The upper portion 312 of the scaffold assembly 302 may be configured to support and position one or more circuit components. As shown in FIG. 3A, the upper portion 312 of the scaffold assembly 302 supports and positions an antenna 318. In certain instances, positioning of the antenna 318 increases the functionality thereof by spatially arranging the broadcast direction(s) with respect to a receiving device configured to communicate with the antenna 318. As a result, and as shown in FIG. 3A, the antenna 318 may be at least partially circumferentially arranged around an exterior section of the upper portion 312 of the scaffold assembly 302. In certain instances, the positioning of the antenna 318 in this manner may allow for maximizing the directional broadcast of the antenna while minimizing interference that may result from integrated circuitry, contained within the core assembly 304, which controls the antenna 318 broadcast. Other arrangements of the antenna 318 are also contemplated. For instance, the antenna 318 may be provided over a lesser or greater surface area of the upper portion 312 of the scaffold assembly 302. Further, the antenna 318 may be embedded in the upper portion 312 of the scaffold assembly 302 to allow for further protection of the antenna 318 by the scaffold assembly 302. Further yet, the antenna 318 may be arranged along the sides of the intermediate portion 314 of the scaffold assembly 302. The antenna 318 may also be formed as a continuous or discontinuous structure.

Similar to the upper portion 312, the intermediate portion 314 of the scaffold assembly 302 may be configured to support and position a circuit component. As shown in FIG. 3A, the intermediate portion 314 of the scaffold assembly 302 supports and positions an electrode 320. In the illustrated embodiments, the electrode 320 is provided on the first surface 302A of the scaffold assembly 302. In embodiments, the electrode 320 may be secured in place on the scaffold assembly 302 by a push-in connection. The push-in connection may be accomplished by use of one or more push-in connectors 324, 326, 328 that secure the electrode 320. The push-in connectors 324, 326, 328 surround exterior portions of the electrode 320. In other embodiments, the scaffold assembly 302 may not include the push-in connectors 324, 326, 328. Rather, the electrode 320 may include extensions, and the scaffold assembly 302 may include corresponding voids or gaps. A friction fit connection may be provided between these elements of the electrode 320 and the scaffold assembly 302 to secure the two together.

The scaffold assembly 302 may position and support the electrode 320 relative to the antenna 318. In certain instances, the antenna 318 may, in part, circumferentially surround the electrode 320. Further and in certain instances, the functionality of the electrode 320 may be enhanced by positioning the electrode to contact or be flush with the first surface 308 of the housing 306.

Figure 3B:
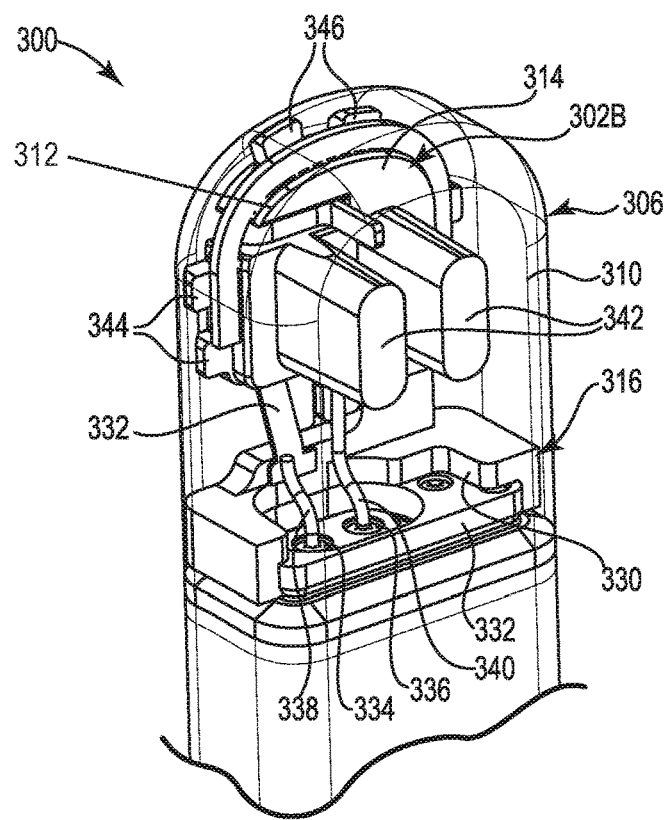
FIG. 3B is a back-facing view of the header and scaffold assembly shown in FIG. 3A, in accordance with embodiments of the disclosure.

FIG. 3B is a back-facing perspective view of the header 300 and scaffold assembly 302 shown in FIG. 3A, in accordance with embodiments of the disclosure. In certain instances, the lower portion 316 of the scaffold assembly 302 is configured to interface with the core assembly 304. The lower portion 316 may include a first mating feature 330 and the core assembly 304 may include a second mating feature 332. The first mating feature 330 and the second mating feature 332 include one or more corresponding surfaces that engage to provide the interface between the scaffold assembly 302 and the core assembly 304. In certain instances, the first mating feature 330 and the second mating feature 332 may interface and provide a frictional fit to secure the scaffold assembly 302 together with the core assembly 304. In addition, an adhesive may be provided on one or more of the first mating feature 330 and the second mating feature 332 to secure the scaffold assembly 302 together with the core assembly 304.

The core assembly 304 may include one or more conduits 334, 336 that provide a feedthrough for at least one electrical connector or interconnect. As shown, two interconnects 338, 340 are provided and feed through the conduits 334, 336 along the second surface 302B of the scaffold assembly 302. Each of the interconnects 338, 340 electrically connects a circuit component positioned and supported by the scaffold assembly 302 to the integrated circuitry contained within the core assembly 304. In certain instances, the interconnects 338, 340 electrically connect with the circuitry components on the backside of the scaffold assembly 302, as is shown in FIG. 3B. More specifically, one interconnect 338 electrically connects the portion 322 of the electrode 320 that passes from the front facing portion of the scaffold assembly 302 to the back facing portion of the scaffold assembly 302, and another interconnect 340 provides a connection between the antenna 318 and the integrated circuitry contained within the core assembly 304. The functionality of the antenna 318 is controlled by integrated circuitry housed within the core assembly 304. The antenna 318 is electrically coupled to integrated circuitry contained within the core assembly 304 via the interconnect 340. Similarly, the functionality of the electrode 320 is controlled by integrated circuitry housed within the core assembly 304, and the electrode 320 is electrically coupled to the integrated circuitry via the interconnect 338.

In certain instances, the second surface 302B of the scaffold assembly 302 may contact the second surface 310 of the housing 306. As shown, the scaffold assembly 302 includes an extension 342 that is provided to contact the second surface 310 of the housing 306. The extension 342 may include a single block structure, two separate (as shown), or three or more structures to support the scaffold assembly 302 against the second surface 310 of the housing 306. The extension 342 may enhance the ability of the scaffold assembly 302 to position and support the electrode 320. In addition, the intermediate portion 314 and/or the lower portion 316 of the scaffold assembly may include one or more side support members 344 and upper support members 346. The side support members 344 and the upper support members 346 may contact the internal surfaces of the housing 306 to further ensure that the scaffold assembly 302 resists movement resulting from normal bodily movement when implanted in a patient and during the implantation procedure. The side support members 344 and the upper support members 346 may also further facilitate protection and/or positioning of the antenna 318.

The illustrative components shown in FIG. 3A and FIG. 3B are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in FIG. 4A and FIG. 4B (discussed in further detail below) may be, in embodiments, integrated with various other components depicted therein (and/or components not illustrated), all of which are considered to be within the ambit of the disclosed subject matter. For example, the electrode 320 may be secured to the scaffold assembly 302 using a clip. The scaffold assembly 302 may include further extensions to help support and contact portions of the housing 306. The scaffold assembly 302 may also, or alternatively, include addition circuit components (such as an additional electrode) and interconnects. In embodiments, each of the elements of the scaffold assembly 302 may be formed as a one-piece structure. Such a structure may be formed using an injection molding process, from pre-molded plastic, and/or formed of a like material and/or like process.

Figure 4A:
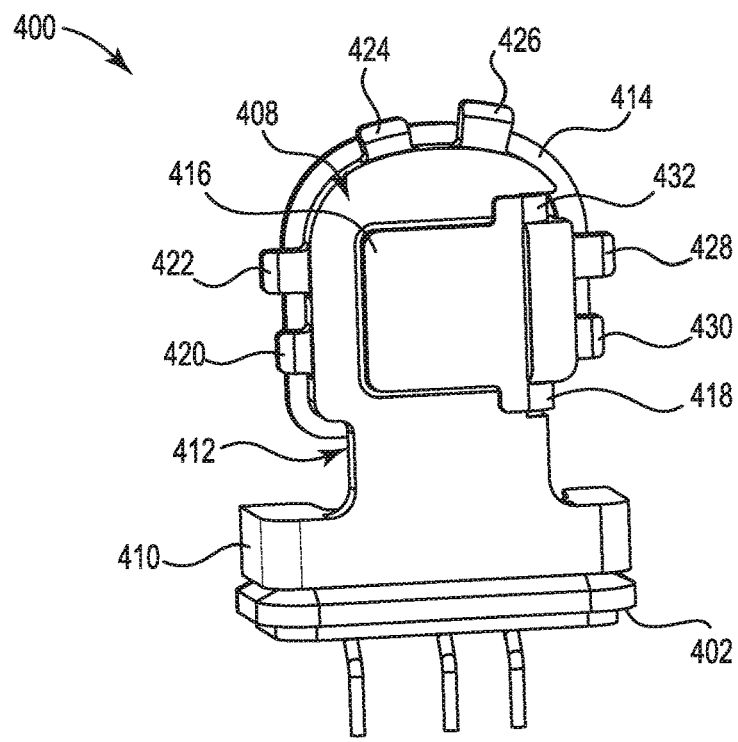
FIG. 4A is a front-facing view of another scaffold assembly and core assembly, in accordance with embodiments of the disclosure.
Figure 4B:
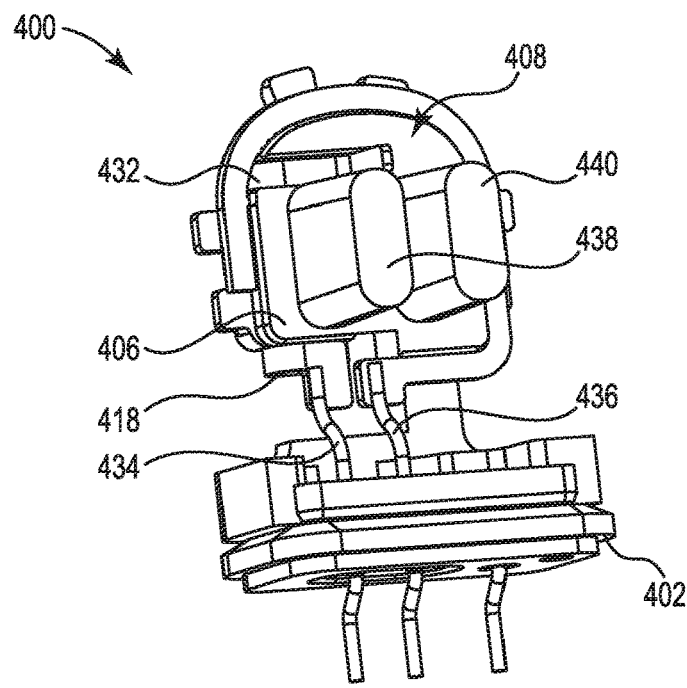
FIG. 4B is a back-facing view of the scaffold assembly and the core assembly shown in FIG. 4A, in accordance with embodiments of the disclosure.

FIG. 4A is a front-facing perspective view of another scaffold assembly 400 and core assembly 402, in accordance with embodiments of the disclosure. The scaffold assembly 400 interfaces with a core assembly 402, both of which may be provided as part of an IMD, for example, as discussed above with reference to FIG. 1 and FIG. 2. As shown in FIG. 4A, the scaffold assembly 400 includes a front facing portion 404 and a rearward facing portion 406 (as is shown in FIG. 4B and discussed in further detail below). In addition, the scaffold assembly 400 may include an upper portion 408, a lower portion 410, and an intermediate portion 412.

The scaffold assembly 400 may support and position various circuit components. For example, the scaffold assembly 400 may be configured to support an antenna 414 and an electrode 416. The antenna 414 is shown arranged at the upper portion 408 of the scaffold assembly 400, and the electrode 416 is shown arranged on front facing portion 404 at the intermediate portion 412 of the scaffold assembly 400. In addition, the electrode 416 may include portions 418, 432 that extend from the front facing portion 404 to the rearward facing portion 406 of the scaffold assembly 400. These portions 418, 432 may function to secure the electrode 416 to the scaffold assembly 400. More specifically, the portions 418, 432 of the electrode 416 may function as clips that secure the electrode 416 to the scaffold assembly 400. The portions 418, 432 of the electrode 416 may wrap around the scaffold assembly 400 from the front facing portion 404 to the rearward facing portion 406, and may form a friction fit with the scaffold assembly 400 to secure the electrode 416 thereto. In certain instances, the scaffold assembly 400 may include a single clip or more than one clip.

In certain instances, one or more of the upper portion 408 and the intermediate portion 412 of the scaffold assembly 400 may include features that may be provided to support and position the circuit components. As shown, the positioning of the antenna 414 on the scaffold assembly 400 is about the upper portion 408 and the intermediate portion 412 of the scaffold assembly 400. In order to maintain the antenna 414 in the appropriate position, the scaffold assembly 400 may include one or more clasps 420, 422, 424, 426, 428, 430. The clasps 420, 422, 424, 426, 428, and 430 may assist in the positioning of antenna 414 on the scaffold assembly 400 during manufacture, and may mitigate against movement of the antenna 414.

FIG. 4B is a back-facing perspective view of the scaffold assembly 400 and the core assembly 402 shown in FIG. 4A, in accordance with embodiments of the disclosure. As shown, the antenna 414 wraps around the intermediate portion 412 of the scaffold assembly 400, and also at least partially surrounds the electrode 416. In certain instances, the antenna 414 and the electrode 416 may be in a common plane such that they are vertically aligned along the scaffold assembly 400. In addition, the antenna 414 extends toward the core assembly 402 longitudinally along the border between the lower portion 410 and the intermediate portion 412 of the scaffold assembly 400. The antenna 414 is electrically coupled to integrated circuitry (not shown) contained within the core assembly 402 by an interconnect 436. The integrated circuit arranged within the core assembly 402 may be configured to prompt the antenna 414 to communicate with a receiving device (shown in FIG. 1). Interconnect 434 is provided to similarly electrically connect the electrode 416 to the integrated circuit arranged within the core assembly 402. In certain instances, the portion 418 of the electrode 416 is also electrically conductive and may function both as a mechanism to secure the electrode 416 to the scaffold assembly 400, and to provide a conductive portion to allow the electrode 416 to electrically connect to the integrated circuitry. Interconnects 434, 436 may be connected to the circuitry components by spot-welding, parallel gap welding, and/or similar process.

The rearward facing portion 406 of the scaffold assembly 400 also may include extensions 438, 440 that enhance the structural stability of the scaffold assembly 400. When the scaffold assembly 400 is provided within a housing of a header (e.g., as shown in FIG. 2A and FIG. 2B), the extensions 438, 440 may contact an internal surface of the housing. In other instances, the extensions 438, 440 may provide a counterbalance to elements provided on the front facing portion 404 of the scaffold assembly 400.

The illustrative components shown in FIG. 4A and FIG. 4B are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in FIG. 3A and FIG. 3B may be, in embodiments, integrated with various other components depicted therein (and/or components not illustrated), all of which are considered to be within the ambit of the disclosed subject matter. For example, the scaffold assembly 302 may include further extensions to help support and contact portions of the housing 306, or may also include additional circuit components (such as an additional electrode) and interconnects. For example, a housing 306 may be provided over the scaffold assembly 400, the electrode 416 may include a push-in design, and/or the core assembly 402 may include conduits as described with reference to FIG. 3A and FIG. 3B.

Figure 5A:
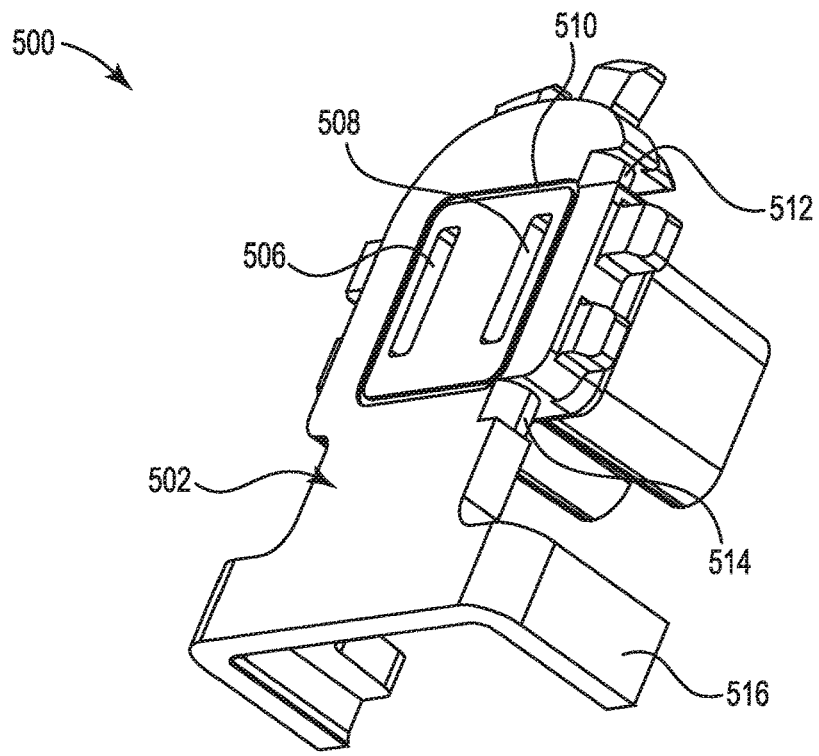
FIG. 5A is a front-facing view of a scaffold assembly, in accordance with embodiments of the disclosure.

FIG. 5A is a front-facing perspective view of a scaffold assembly 500, in accordance with embodiments of the disclosure. A frontward facing portion/surface 502 of the scaffold assembly 500 may include a number of different features that may position and support one or more circuit elements and secure the elements to the scaffold assembly 500. For example, the frontward facing portion/surface 502 may be provided with one or more recesses 506, 508. The one or more recesses 506, 508 allow for attachment of a circuit component, such as an electrode having a push-in securement design, to the scaffold assembly 500 (e.g., as described with reference to FIG. 3A and FIG. 3B). The circuit component may include corresponding extensions or structures that friction fit within the recesses 506, 508 to secure the circuit component to the scaffold assembly 500. The recesses 506, 508 may be rectangular in shape, as shown, or the recesses 506, 508, may be cylindrical, oblong, triangular, or the like. In addition, the frontward facing portion/surface 502 of the scaffold assembly 500 may include a boundary recess 510 that functions to secure a circuit component to the scaffold assembly 500. Securing the circuit components to the scaffold assembly 500 may be enhanced by providing an adhesive within the recesses 506, 508 or boundary recess 510.

The scaffold assembly 500 may also include one or more hinges 512, 514. Similar to the recesses 506, 508, 510, the hinges 512, 514 allow for attachment of a circuit component, such as an electrode having a clip-in securement design, to the scaffold assembly 500 (e.g., as described with reference to FIG. 4A and FIG. 4B). The circuit component may include a structure, such as a bracket or the like, that friction fits over one or more of the hinges 512, 514. Depending on the design of the specific circuit component, the scaffold assembly 500 may include one or more of the recesses 506, 508, 510 and one or more of the hinges 512, 514, only one or more of the recesses 506, 508, 510, or only one or more of the hinges 512, 514.

In certain instances, a bottom portion 516 of the scaffold assembly 500 may be provided to interface with a core assembly (as described above). In addition, the bottom portion 516 of the scaffold assembly 500 may provide a base from which the remaining portions of the scaffold assembly 500 may extend.

Figure 5B:
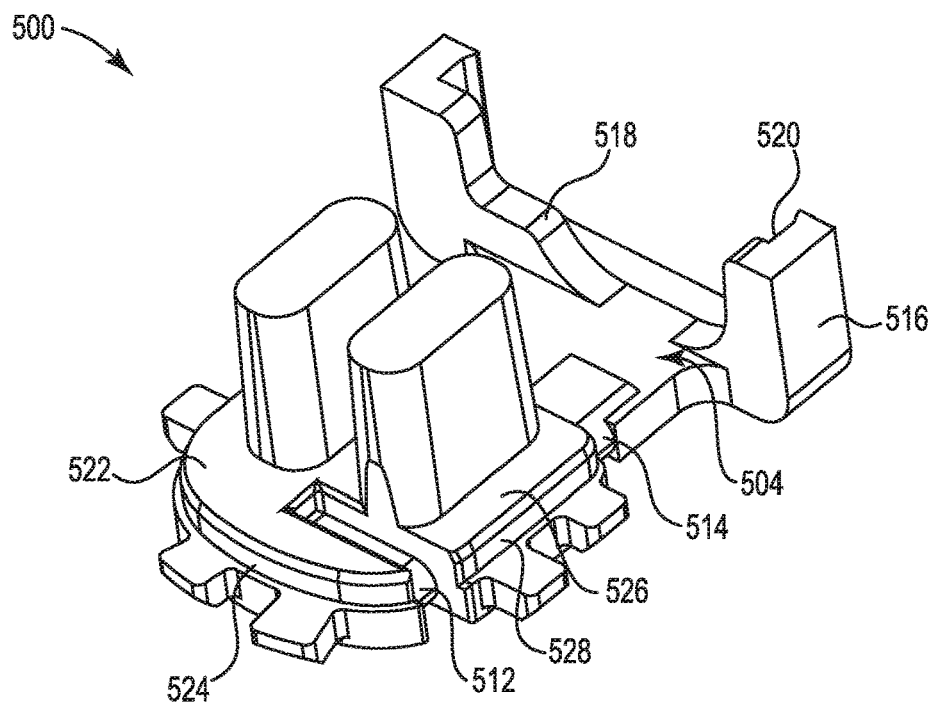
FIG. 5B is a back-facing view of the scaffold assembly shown in FIG. 5A, in accordance with embodiments of the disclosure.

FIG. 5B is a back-facing perspective view of the scaffold assembly shown in FIG. 5A, in accordance with embodiments of the disclosure. A rearward facing portion/surface 504 of the scaffold assembly 500 includes various features that allow for increased manufacturability and functionality of components. For instance, the bottom portion 516 of the scaffold assembly 500 may include a mating feature or mating surface 518. The mating feature or mating surface 518 may be formed of any shape, such as the unique shape shown, or as a symmetric curved shape, an asymmetric curved shape, a symmetrical box shape, an asymmetric box shape, and/or the like. In certain instances, the mating feature or mating surface 518 may have a corresponding second mating feature or mating surface that is associated with a core assembly (as described above with reference to FIG. 3A and FIG. 3B). The second mating feature or mating surface that is associated with a core assembly may include a lesser depth or height than the mating feature or mating surface 518 associated with the scaffold assembly 500. Thus, the mating feature or mating surface 518 may be slid or disposed over the second mating feature or mating surface that is associated with a core assembly.

More specifically and as shown in FIG. 5B, the mating feature or mating surface 518 includes a lip or flange 520 that is configured to engage a corresponding lip or flange provided with the second mating feature or mating surface that is associated with a core assembly. The lip or flange 520 may be provided only at end portions of the mating feature or mating surface 518, or the lip or flange 520 may be provided along the entire circumference of the mating feature or mating surface 518.

In certain instances, an upper portion 522 of the scaffold assembly may include a surface 524 offset from the rearward facing portion/surface 504 of the scaffold assembly. In addition, an intermediate portion 526 of the scaffold assembly 500 may include a surface 528 offset from the rearward facing portion/surface 504 of the scaffold assembly. The surface 528 may provide a recess for mounting a circuit component (such as an antenna). The circuit component may be provided along a portion or the entirety of the surface 528.

Embodiments of the scaffold assembly 500 allow for repeatable manufacturing and assembly when used in connection with an IMD. The scaffold assembly 500 may position and support circuit components in an advantageous position (relative to one another), and may mitigate against movement or shifting that may result in improper functionality.

Figure 6:
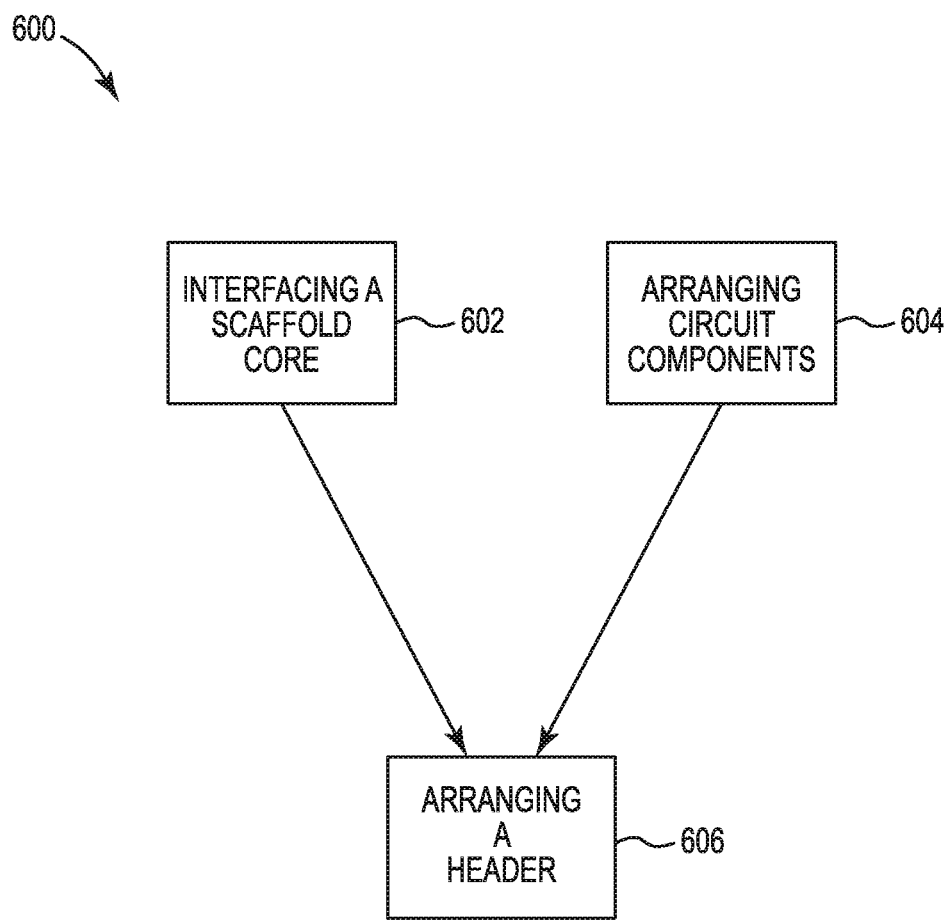
FIG. 6 is a flowchart illustrating an example of a method of assembling an IMD including a scaffold assembly, in accordance with embodiments of the disclosure.

FIG. 6 is a flowchart illustrating an example of a method 600 of assembling an implantable medical device (IMD) including a scaffold assembly, in accordance with embodiments of this disclosure. At block 602, the method 600 includes interfacing a scaffold assembly with a core assembly of an IMD. As described above with reference to FIG. 5A and FIG. 5B, each of the scaffold assembly and the core assembly may include a respective mating feature. The mating features may include corresponding or mirrored faces, such that the respective mating features may interface and frictionally fit together to secure the scaffold assembly and the core assembly together. In certain instances, the core assembly, including integrated circuitry contained therein, may be fully assembled. As described above, one or more interconnects may be provided to electrically couple the integrated circuitry to circuit components supported and positioned by the scaffold assembly. Thus, in certain instances, the scaffold assembly may be interfaced with the core assembly with the core assembly having interconnects provided therethrough.

At block 604, the method 600 includes arranging a first circuit component and a second circuit component on portions of the scaffold assembly. The scaffold assembly may be configured to position and support the first circuit component relative to the second circuit component. In certain instances, the step shown at block 604 may be performed prior to interfacing the scaffold assembly with the core assembly. In addition, the steps shown at block 602 and block 604 may be performed as part of the same manufacturing step. In certain instances, the step shown at block 604 further includes electrically connecting the first circuit component and the second circuit component to an integrated circuit arranged within the core assembly. This may include welding the first circuit component and the second circuit to respective electrical connectors coupled to the integrated circuit.

At block 606, the method 600 includes arranging a header assembly over and around the scaffold assembly and interfacing the header assembly with the core assembly. The header may include an exterior surface and an interior surface, with the interior surface providing an interior space for the scaffold assembly. In certain instances, arranging the header assembly may include arranging one or more of the circuit elements to be flush with the exterior surface of the header. In this manner, one or more of the circuit elements may form a part of the exterior surface of the header. More specifically, one or more of the circuit elements may be an electrode. The electrode may be arranged to be flush with the exterior surface of the header to allow for the electrode to have contact with a patient's internal physiology when the IMD is implanted in the patient.

Figure 7A:
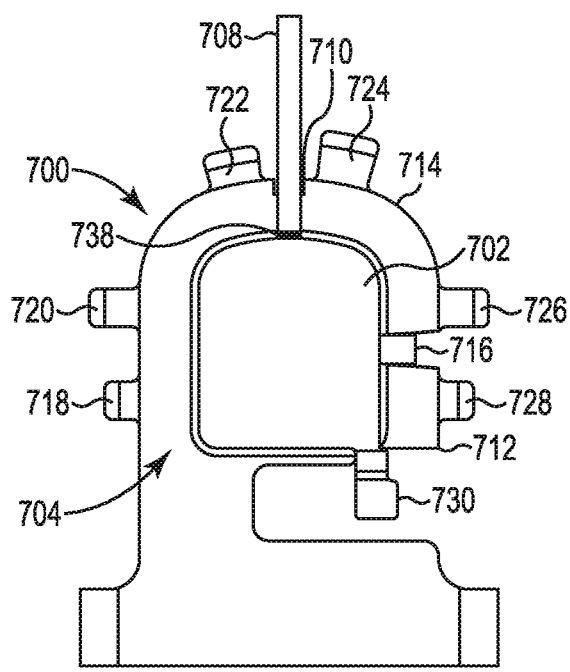
FIG. 7A is a front-facing view of another scaffold assembly and electrode, in accordance with embodiments of the disclosure.

FIG. 7A is a front-facing view of another scaffold assembly 700 assembly and electrode 702, in accordance with embodiments of the disclosure. The scaffold assembly 700 interfaces with a core assembly (not shown) such as those shown and detailed above with reference to, for example, FIGS. 3A-B and FIGS. 4A-B. The scaffold assembly 700, core assembly, and electrode 702 may be provided as part of an IMD, for example, as discussed above with reference to FIG. 1 and FIG. 2. As shown in FIG. 7A, the scaffold assembly 700 includes a front facing portion 704 and a rearward facing portion 706 (as is shown in FIG. 7B and discussed in further detail below).

In certain instances, the electrode 702 may be provided with a break-away section 708. The break-away section 708 may assist in aligning the electrode 702 and during assembly. Precise alignment and positioning of the electrode 702 may be important because, as noted above, the scaffold assembly 700 may support and position additional and other various circuit components (such as antenna). The positioning and support of the electrode 702 and other various circuit components (not shown in FIG. 7A) can affect the performance of an IMD. For instance, adequate spacing and precise spacing between the electrode 702 and other various circuit components may provide for controlled and predictable performance of the circuit component by avoiding (or minimizing) capacitive coupling between the elements, and also avoiding shorting. Thus, in positioning the electrode 702 on the scaffold assembly 700, the break-away section 708 may be aligned with an alignment notch 710 on the scaffold 702. As shown, the alignment notch 710 is defined in an upper section 712 along a perimeter 714 of the scaffold assembly 700. The alignment portion 710 may be provided along any portion of the perimeter 714 of the upper section 712 of the scaffold assembly 700.

Figure 7B:
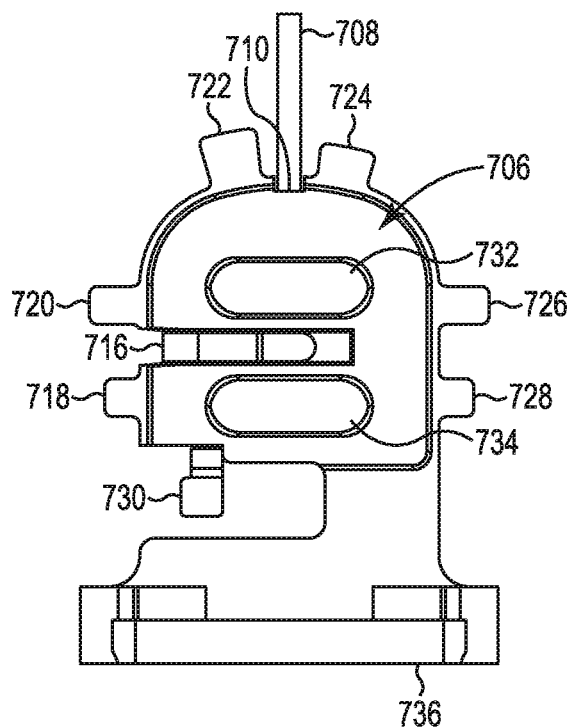
FIG. 7B is a back-facing view of the scaffold assembly and electrode shown in FIG. 7A, in accordance with embodiments of the disclosure.

In positioning the electrode 702 on the scaffold assembly 700, the break-away section 708 may be aligned within the alignment notch 710, as is shown in FIGS. 7A and 7B. The break-away section 708 is releasably secured or couple to the electrode 702 via a break-away tab 738. The break-away tab 738 may be formed of a different material (such as an adhesive) than the break-away section 708, or the break-away tab 738 may be of the same material as the break-away section 708 but may have, for example, a lesser width or structural strength. In this manner, after positioning the electrode 702 on the scaffold assembly 700, a manufacturer may manipulate the break-away section 708 such that the break-away tab 738 breaks or splits from the electrode 702, and the break-away section 708 and the break-away tab 738 are removed from the electrode 702. The break-away section 708 and the alignment notch 710 of the scaffold assembly 700 provide a visual indicator, which may serve to facilitate alignment of the electrode 702 on the scaffold assembly 700.

Additional sections 718, 720, 722, 724, 726, and 728 of the scaffold assembly 700 may assist in the positioning of an antenna or other circuit element on the scaffold assembly 700 during manufacture, and may mitigate against movement of the antenna. In addition, a clip 716, which is formed as a portion of the electrode 702, secures the electrode 702 in place on the scaffold 702. The clip 716 may be seen in both FIG. 7A and FIG. 7B The scaffold 700 may include an edge (not shown and covered by the clip 716) that corresponds to a shape of the clip 716. As a result, the clip 716 may be slid over the edge of the scaffold 700 by which the electrode 702 is held in place. A connection point 730, which is formed as a portion of the electrode 702, may be seen in both FIG. 7A and FIG. 7B. This portion 730 of the electrode may serve to provide as a connection point for the electrode 702 to integrated circuitry of the IMD.

Figure 7C:
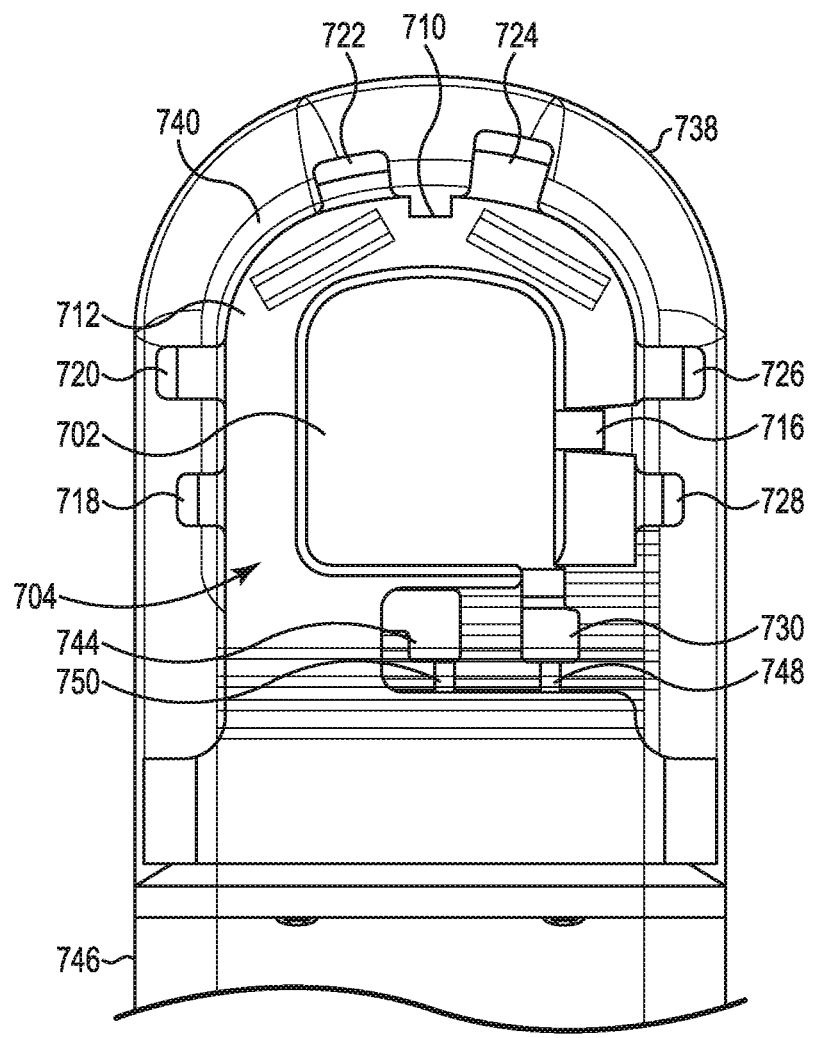
FIG. 7C is a front-facing view of the scaffold assembly and the electrode shown in FIGS. 7A and 7B further including a header, in accordance with embodiments of the disclosure.

FIG. 7B is a back-facing view of the scaffold assembly 700 and the electrode 702 shown in FIG. 7A. The break-away section 708 can be seen aligned with the alignment notch 710 of the scaffold assembly 700. In addition, the clip 716 secures the electrode 702 onto the scaffold assembly 700 by a friction fit connection on the rearward facing portion 706 (and the front facing portion 704) of the scaffold assembly 700. Further, the scaffold assembly 700 may include extensions 732, 734 that enhance the structural stability of the scaffold assembly 700. When the scaffold assembly 400 is provided within a housing of a header (as shown in FIG. 7C), the extensions 732, 734 may contact an internal surface of the housing. In other instances, the 732, 734 may provide a counterbalance to elements provided on the front facing portion 704 of the scaffold assembly 700. Also shown in FIG. 7B is a mating feature or mating surface 736. The mating feature or mating surface 736 may be formed of any shape. In certain instances, the mating feature or mating surface 736 may have a corresponding second mating feature or mating surface that is associated with a core assembly (as described above with reference to FIG. 3A and FIG. 3B). The mating feature or mating surface 736 may be slid or disposed over the second mating feature or mating surface that is associated with the core assembly to and friction fit the scaffold assembly 700 to the core assembly.

FIG. 7C is a front-facing view of the scaffold assembly 700 and the electrode 702 shown in FIGS. 7A and 7B further including a header housing 738 (shown as transparent), in accordance with embodiments of the disclosure. FIG. 7C shows a portion of a fully-assembled IMD header. The electrode 702 is shown assembled on the scaffold assembly 700 without the break-away section 708 and held in place by the clip 716. The alignment notch 710 of the scaffold assembly 700 is also shown in FIG. 7C. In addition, the scaffold assembly 700 is also shown supporting an antenna 740. The antenna 740 is shown supported and positioned by the additional sections 718, 720, 722, 724, 726, and 728 of the scaffold 702. The header housing 738 covers the scaffold assembly 700 (including the electrode 702 and the antenna 740), and interfaces with a core assembly 746.

As noted above (with reference to FIG. 2), the core assembly 746 may include integrated circuitry. The integrated circuitry may control the functionality of the electrode 702 and the antenna 740. Interconnects 748, 748 may be configured to connect the electrode 702 and the antenna 740 to the integrated circuitry contained within the core assembly 746. The interconnects 748, 748 connect to a portion 744 of the antenna 740, and the portion 730 of the electrode 702 that passes from the front facing portion 704 to a rearward facing portion 706.

Figure 8A:
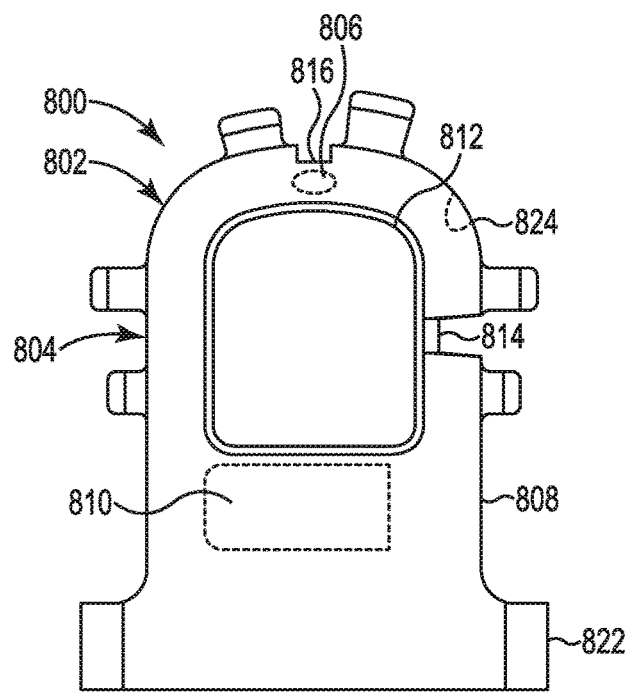
FIG. 8A is a front-facing view of another scaffold assembly, in accordance with embodiments of the disclosure.
Figure 8B:
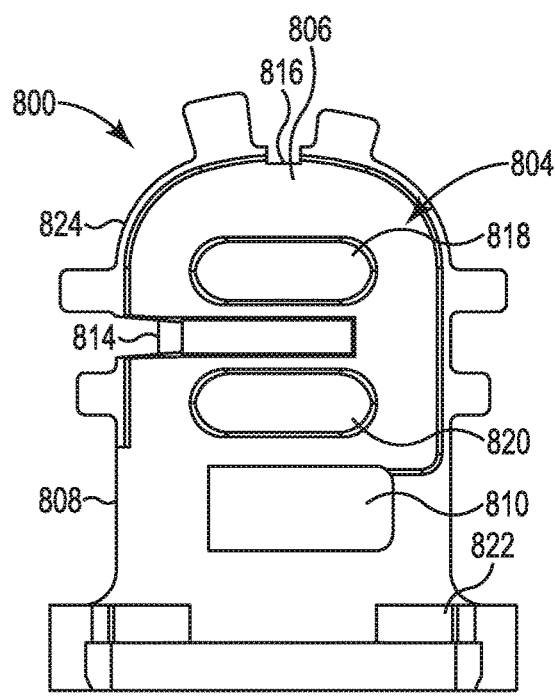
FIG. 8B is a back-facing view of the scaffold assembly shown in FIG. 8A, in accordance with embodiments of the disclosure.

FIG. 8A is a front-facing view of another scaffold assembly 800, in accordance with embodiments of the disclosure. In addition, FIG. 8B is a back-facing view of the scaffold assembly 800 shown in FIG. 8A, in accordance with embodiments of the disclosure. FIGS. 8A and 8B show a variety of different aspects that may or may not be included with the scaffold assembly 800. In addition, each of these aspects may include a number of different shapes and sizes in order to accommodate a variety of different electrodes (such as those shown in FIGS. 9-15) having different shapes and sizes.

As shown in FIGS. 8A and 8B, a perimeter 802 of an upper section 804 of the scaffold assembly 800 includes an alignment notch 816, as described above in detail with reference to FIGS. 7A-7C. The alignment notch 816 may be located at any portion along the perimeter 802 of the upper section 804 of the scaffold assembly 800. The alignment notch 816 aligns with a break-away section on an electrode, therefore, if the electrode has a break-away section that projects horizontally as shown in FIG. 11 (as opposed to vertically as shown in FIG. 7A-7B), the alignment notch 816 will be located along a side portion (as opposed to top or bottom) of the perimeter 802.

Figure 12:
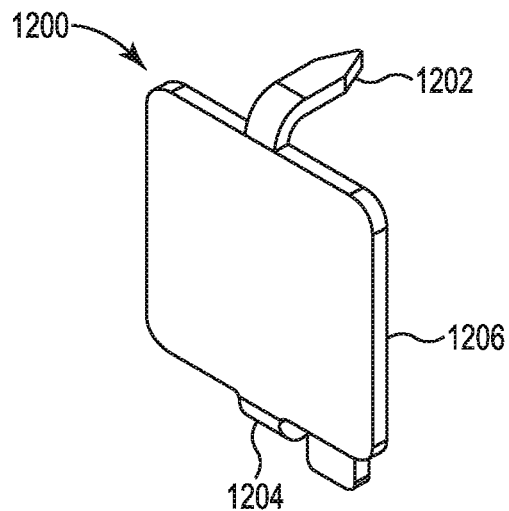
FIG. 12 is a perspective view of another example electrode, in accordance with embodiments of the disclosure.
Figure 13:
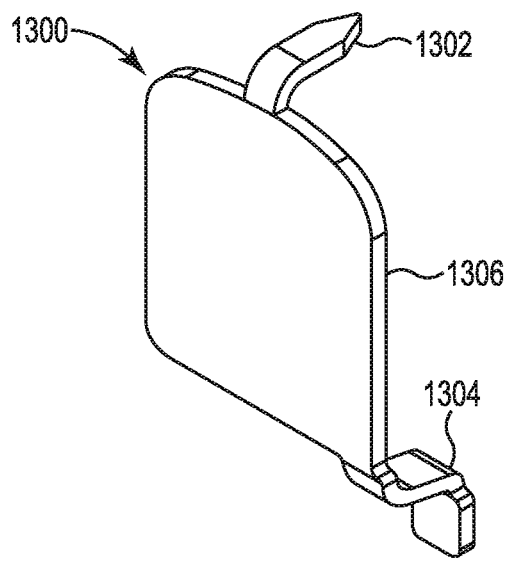
FIG. 13 is a perspective view of another example electrode, in accordance with embodiments of the disclosure.

The scaffold assembly 800 may also include an optional void or opening portion 806. The optional void or opening portion 806 may provide an additional mechanism for securing an electrode to the scaffold assembly 800. The optional void or opening portion 806, for instance, may interface with an attachment projection of an electrode (as shown in FIGS. 12-13). The scaffold assembly 800 may also include a portion 814 that allows an electrode with a clip-like portion (as shown in FIGS. 7A-7C) to interface therewith. Further and as shown in FIG. 10, electrodes may include multiple clip-like portions. Therefore, the scaffold assembly 800 may include an additional portion 824 to interface with the additional clip-like portion. Both portions 814, 824 of the scaffold assembly 800 may be located along any portion of the perimeter 802 so long as the portions 814, 824 correspond to clip-like portions of an electrode. The scaffold assembly 800 may also include a groove 812 that corresponds to an outer perimeter of an electrode.

Further, the scaffold assembly 800 may include a vertical support 808 that connects the upper section 804 to a lower section 822. The vertical support 808 may be positioned and have a width to allow an element of an electrode to pass through an opening 810 in the scaffold assembly 800. In certain instances, however, the scaffold assembly 800 may not include an opening 810. Further yet, extensions 818, 820 optionally provided with the scaffold assembly 800 may be aligned with a horizontal axis of the scaffold assembly 800 (as is shown in FIG. 8B) or may also be aligned with a vertical axis of the scaffold assembly 800.

FIG. 9 is a perspective view of an example electrode 900, in accordance with embodiments of the disclosure. The electrode 900 shown in FIG. 9 includes portion 902 that is provided to pass from a front-side of a scaffold assembly to a backside of the scaffold assembly (e.g., as shown in FIGS. 7A-B) to allow for connection to interconnects. The portion 902 may be friction fit with a corresponding portion of the scaffold assembly to secure the electrode 900 thereto.

FIG. 10 is a perspective view of another example electrode 1000, in accordance with embodiments of the disclosure. The electrode 1000 includes two clip-like portions 1002, 1004. The clip-like portions 1002, 1004 may interface with a portion on a scaffold assembly such as those as elements 814 and 824 in FIGS. 8A-8B. In addition, one or more of the clip-like portions 1002, 1004 may serve as an electrical contacting point for interconnects that are electrically coupled to integrated circuitry.

FIG. 11 is a perspective view of another example electrode 1100, in accordance with embodiments of the disclosure. The electrode 1100 includes a break-away section 1102, a clip-like portion 1104, and an addition portion 1106 that provides an electrical contacting point for interconnects that are electrically coupled to integrated circuitry. As described in detail above with reference to FIG. 7A-7C, for example, the break-away section 1102 may be configured to position and align the electrode 1100 on a scaffold assembly. In addition, the clip-like portion 1104 may be configured to maintain the electrode 1100 in the aligned position on the scaffold assembly during and after the break-away section 1102 is removed from the electrode 1100.

FIG. 12 is a perspective view of another example electrode 1200, in accordance with embodiments of the disclosure. The electrode 1200 includes an attachment projection 1202 and an addition portion 1204 that provides an electrical contacting point for interconnects that are electrically coupled to integrated circuitry. The attachment projection 1202 may be configured to secure the electrode 1200 to a scaffold assembly via a void, as shown and described in FIGS. 8A-8B. FIG. 13 is a perspective view of another example electrode 1300, in accordance with embodiments of the disclosure. The electrode 1300 includes an attachment projection 1302 and an addition portion 1302 that provides an electrical contacting point for interconnects that are electrically coupled to integrated circuitry. As compared to FIG. 12, the addition portion 1302 is laterally offset along a perimeter 1306 of the electrode 1300 as compared to the position of the additional portion 1202 along a perimeter 1206 of the electrode 1200. Similar to the electrode shown in FIG. 12, the attachment projection 1302 may be configured to secure the electrode 1300 to a scaffold assembly via a void, as shown and described in FIGS. 8A-8B.

Figure 14:
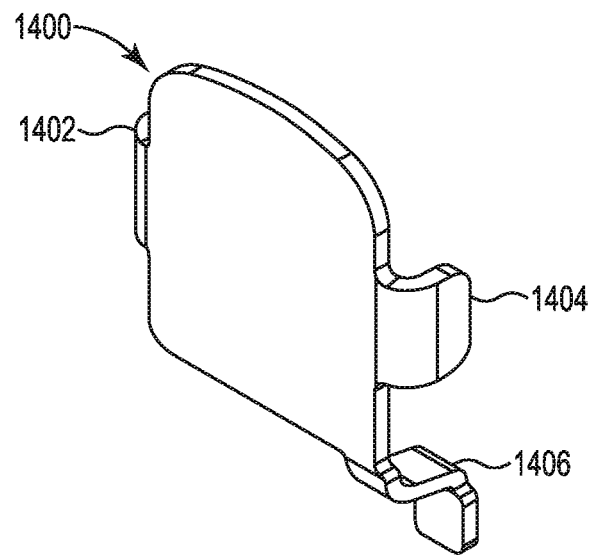
FIG. 14 is a perspective view of another example electrode, in accordance with embodiments of the disclosure.
Figure 15:
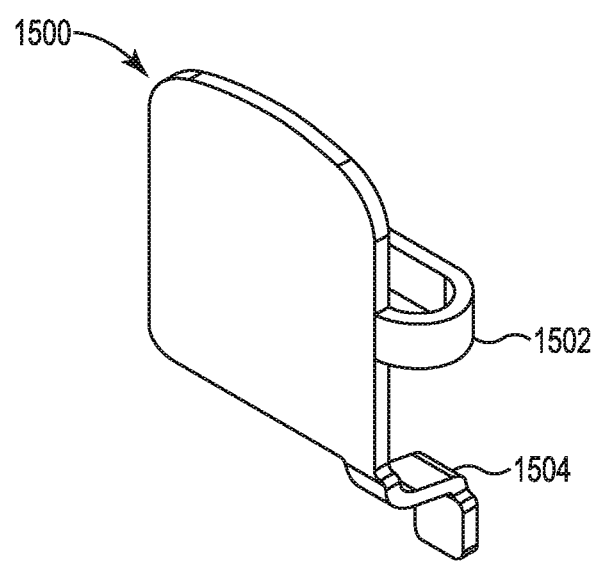
FIG. 15 is a perspective view of another example electrode, in accordance with embodiments of the disclosure.

FIG. 14 is a perspective view of another example electrode 1400, in accordance with embodiments of the disclosure. The electrode 1400 includes two clip-like portions 1402, 1404 for securing the electrode 1400 to a scaffold assembly. In addition, the electrode 1400 includes an additional portion 1406 that provides an electrical contacting point for interconnects that are electrically coupled to integrated circuitry As compared to FIG. 14, FIG. 15 is a perspective view of another example electrode 1500 having a single clip-like portion 1502 and an additional portion 1504 that provides an electrical contacting point for interconnects that are electrically coupled to integrated circuitry, in accordance with embodiments of the disclosure.

Figure 16A:
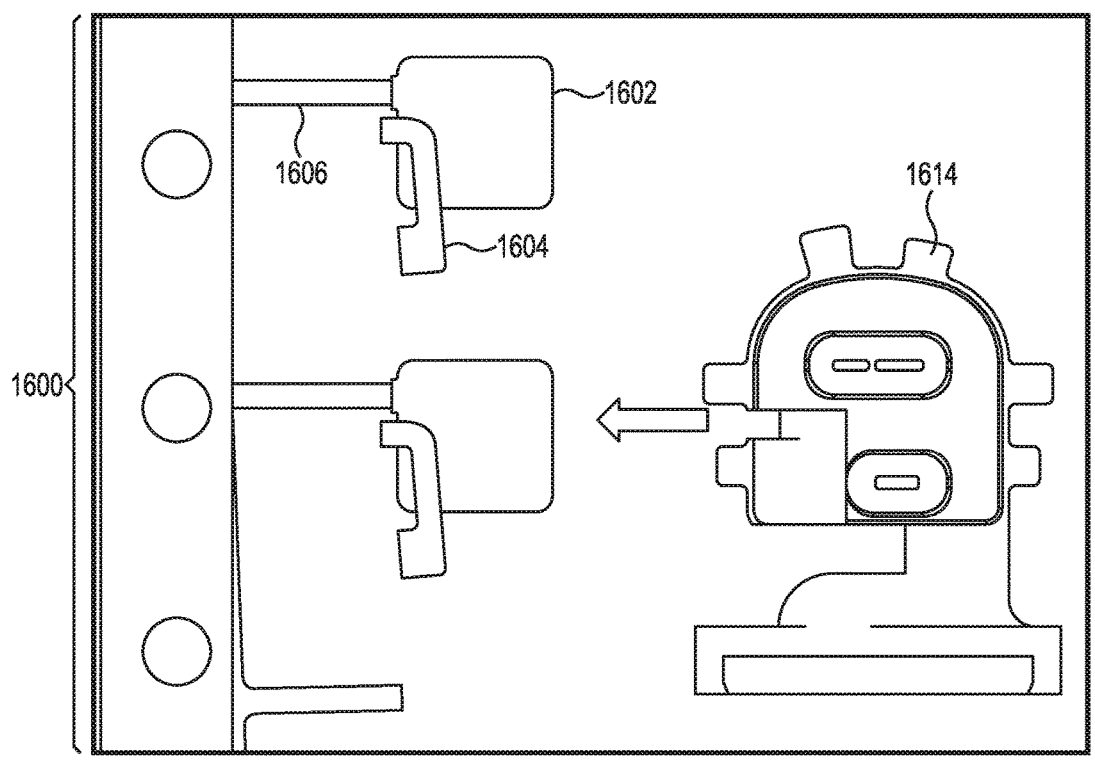
FIG. 16A depicts electrodes secured to a metal strip and a scaffold assembly for assembling one of the electrodes together with the scaffold assembly, in accordance with embodiments of the disclosure.

FIG. 16A depicts electrodes 1602, 1608 coupled to a manufacturing aid 1600, and a scaffold assembly 1614 for assembling one of the electrodes together with the scaffold assembly, in accordance with embodiments of the disclosure. The electrodes 1602, 1608 are shown held together by a manufacturing aid 1600. The manufacturing aid 1600 may comprise the same or similar material as the electrodes 1602, 1608, or may comprise a different (e.g., insulative material). Further yet, the manufacturing aid 1600 and the electrodes 1602, 1608 may be formed from the same piece of material. In addition, although two electrodes 1602, 1608 are shown in FIG. 16A, multiple additional electrodes may be provided with the manufacturing aid 1600. According to embodiments, the manufacturing aid 1600 may be a portion of a metal strip from which the electrodes are progressively stamped, e.g., using a progressive die.

Each of the electrodes 1602, 1608 is provided with a break-away section 1606, 1612. The break-away sections 1606, 1612 are coupled at one end to the manufacturing aid 1600, and at the other end to break-away tabs 1604, 1610, which are in turn coupled to the electrodes 1602, 1608. Although multiple scaffold assemblies may be provided, a single scaffold assembly 1614 is shown in FIG. 16A for simplicity. The scaffold assembly 1614 includes an alignment portion 1616 to aid in positioning the one of the electrodes 1602, 1608 on the scaffold assembly 1614.

Figure 16B:
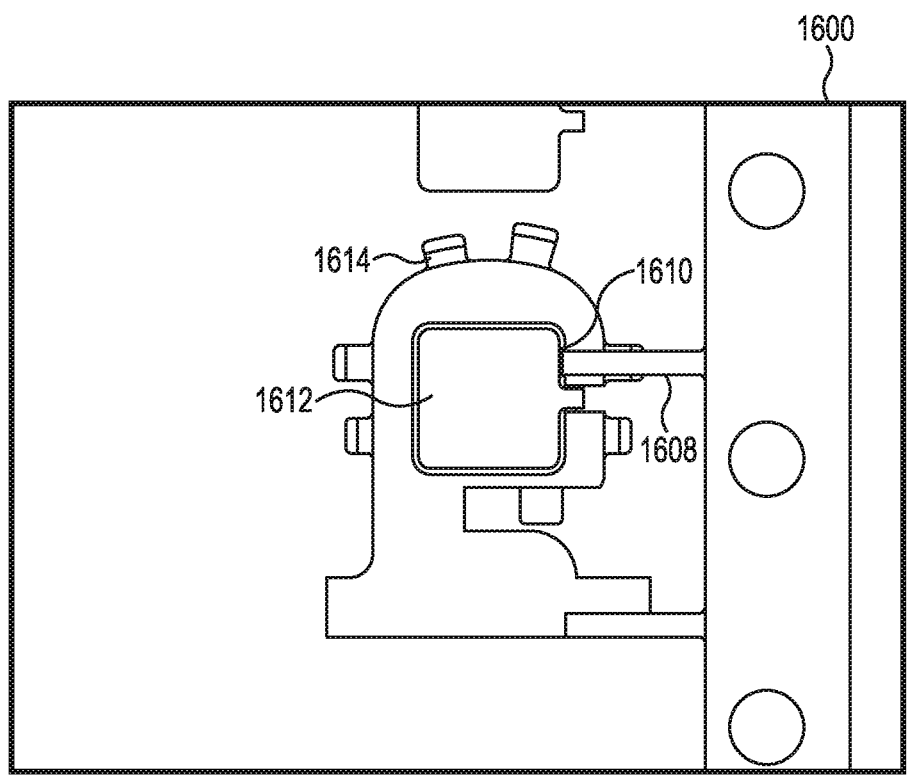
FIG. 16B depicts the scaffold assembly assembled with one of the electrodes, as shown in FIG. 16A, in accordance with embodiments of the disclosure.

FIG. 16B depicts the electrode 1612 assembled together with the scaffold assembly 1614 as shown in FIG. 16A, in accordance with embodiments of the disclosure. The alignment portion 1616 is shown aligned with the break-away section 1608. After the alignment between the electrode 1612 and the scaffold 1614, the break-away section 1608 and the break-away tab 1610 can be removed from the electrode 1612. The break-away section 1608 and the break-away tab 1610 remain with the manufacturing aid 1600. In certain instances, the break-away tab 1610 have a "v" shape or indentation due to a reduced thickness relative to the break-away section 1608. In these instances, the break-away section 1608 and the break-away tab 1610 may be removed by a bend (e.g., between approximately a 45 degree and approximately a 90 degree bend) to remove the electrode 1612 from the scaffold 1614. As would be understood, multiple scaffold assemblies aligned with the multiple electrodes at the same time. Alignment portions provided with each scaffold assembly allows for a manufacturer, either by manual visual inspection or by using an automated procedure, to align multiple scaffold assemblies and electrodes together at the same time.

Various modifications and additions can be made to the exemplary embodiments discussed without departing from the scope of the disclosed subject matter. For example, while the embodiments described above refer to particular features, the scope of this disclosure also includes embodiments having different combinations of features and embodiments that do not include all of the described features. Accordingly, the scope of the disclosed subject matter is intended to embrace all such alternatives, modifications, and variations as fall within the scope of the claims, together with all equivalents thereof.

We claim:

1. An implantable medical device comprising:
    a header and a core assembly, the header comprising an internal portion and an external portion, and the interior portion comprising a first surface and a second surface;
    a first circuit component comprising an antenna and a second circuit component comprising an electrode, the first circuit component and the second circuit component being arranged within the header and the second circuit component includes a break-away section with the break-away section being configured to split from the second circuit component; and
    a scaffold assembly arranged within the header and configured to interface with the core assembly and position and support the first circuit component relative to the second circuit component.

2. The medical device of claim 1, wherein the scaffold assembly is configured to support and position the electrode flush with the first surface of the interior portion of the header.

3. The medical device of claim 1, wherein the scaffold assembly includes a frontward facing portion and a rearward facing portion, and wherein the frontward facing portion is arranged to support the electrode, and the rearward facing portion contacts the second surface of the interior portion of the header.

4. A system comprising:
    a medical device, configured to be implanted within a body of a patient, the medical device, the medical device comprises a header and a core assembly, an antenna arranged within the header and configured to communicate data and an electrode arranged within the header and configured to collect data, and a scaffold assembly arranged within the header and configured to interface with the core assembly and position and support the antenna relative to the electrode with the electrode including a break-away section, the break-away section being configured to split from the electrode after alignment of the electrode on the scaffold; and
    a receiving device configured to receive the data communicated from the implantable medical device.

5. The system of claim 4, wherein the implantable medical device comprises at least one of an implantable diagnostic monitor (IDM), a cardiac pacemaker, an implantable cardioverter defibrillator (ICD) device, and a cardiac resynchronization therapy (CRT) device.

6. The system of claim 4, wherein the scaffold assembly includes a frontward facing portion relative to the header, a rearward facing portion, an upper portion, and a lower portion, and wherein the frontward facing portion is arranged to support the electrode, the rearward facing portion contacts the second surface of an interior portion of the header, and the upper portion is configured to support the antenna.

7. The system of claim 4, wherein the lower portion includes a mating feature configured to interface with the core assembly.

8. The system of claim 7, wherein the mating feature is arranged along the rearward facing portion of the scaffold assembly.

9. The system of claim 4, wherein the implantable medical device further comprises an integrated circuit arranged within the core assembly, wherein the integrated circuit is configured to prompt the antenna to communicate with the receiving device.

* * * * *